United States Patent
Akahori (10) Patent No.: US 8,184,765 B2
(45) Date of Patent: May 22, 2012

(54) RADIOGRAPHY APPARATUS

(75) Inventor: Sadato Akahori, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 25 days.

(21) Appl. No.: 12/923,528

(22) Filed: Sep. 27, 2010

(65) Prior Publication Data

US 2011/0075792 A1 Mar. 31, 2011

(30) Foreign Application Priority Data

Sep. 28, 2009 (JP) ................................. 2009-222251

(51) Int. Cl.
*A61B 6/00* (2006.01)
(52) U.S. Cl. ................................. 378/4; 378/25; 378/26
(58) Field of Classification Search ................ 378/4, 25, 378/26, 37
See application file for complete search history.

(56) References Cited

U.S. PATENT DOCUMENTS

| | | | |
|---|---|---|---|
| 6,707,878 B2 | 3/2004 | Claus et al. | |
| 6,980,624 B2 | 12/2005 | Li et al. | |
| 7,515,682 B2 | 4/2009 | Li et al. | |
| 2003/0095624 A1* | 5/2003 | Eberhard et al. | 378/37 |
| 2005/0213701 A1* | 9/2005 | Sendai | 378/8 |
| 2006/0153434 A1* | 7/2006 | Wang | 382/128 |
| 2006/0269114 A1* | 11/2006 | Metz | 382/131 |
| 2008/0285712 A1* | 11/2008 | Kopans et al. | 378/26 |

OTHER PUBLICATIONS

Takeshi Shiomi "The principle and clinical application of Tomosynthesis" Journal of Japan Society of Medical Imaging and Information Sciences, vol. 24, No. 2, pp. 22-27, 2007.

* cited by examiner

*Primary Examiner* — Alexander H Taningco
(74) *Attorney, Agent, or Firm* — Jean C. Edwards, Esq.; Edwards Neils PLLC

(57) ABSTRACT

A radiation source is moved, relative to a detection means, in a movement range that is calculated based on a desired slice angle with respect to a predetermined base point on a base plane that defines a range of obtaining a slice image of a subject. The radiation source is moved to a plurality of positions, and a plurality of radiographic images of the subject corresponding to the plurality of positions are obtained by irradiating the subject with radiation from the plurality of positions. Further, a slice image of the subject is reconstructed from the plurality of radiographic images. When the slice image is reconstructed, radiographic images to be used to reconstruct the slice image are selected based on a distance from the detection surface of the detection means to a slice plane on which the slice image is to be generated, and the desired slice angle.

9 Claims, 9 Drawing Sheets

RADIOGRAPHY APPARATUS

CROSS-REFERENCE TO RELATED APPLICATIONS

The present application claims priority from Japanese Patent Application No. 2009-222251, filed Sep. 28, 2009, the contents of which are herein incorporated by reference in their entirety.

BACKGROUND OF THE INVENTION

1. Field of the Invention

The present invention relates to a radiography apparatus for performing tomosynthesis radiography to generate slice images of a subject.

2. Description of the Related Art

In recent years, tomosynthesis radiography was proposed to observe affected regions of patients in more detail by a radiography apparatus using X-rays. In tomosynthesis radiography, radiography is performed by moving an X-ray tube to different positions, and by irradiating a subject by the X-ray tube at different angles from the different positions. Further, images obtained by radiography are added to obtain an image in which a desired cross section of the subject is emphasized. In tomosynthesis radiography, the X-ray tube is moved parallel to an X-ray detector, or in such a manner to draw a circle or an ellipse or oval, based on the characteristic of a radiography apparatus and the kind of slice images (tomograms) to be obtained. The subject is radiographed at different radiation angles to obtain a plurality of radiographic images, and a slice image of the subject is reconstructed from the plurality of radiographic images.

In tomosynthesis radiography as described above, a method for obtaining slice images having different slice thicknesses has been proposed. In the method, a plurality of radiographic images are combined by weighted addition and the like to obtain the slice images (please refer to U.S. Pat. No. 7,515,682 (Patent Document 1)). Further, a method for preventing inconsistency at the edges of images and generation of a ghost at a position in which a subject should not be present has been proposed. In the method, a plurality of radiographic images are processed by non-uniform weighted addition (please refer to U.S. Pat. No. 6,980,624 (Patent Document 2)). Further, a method using order statics, such as a minimum value, a maximum value and a median, in addition to an average value has been proposed to reconstruct an image from radiographic images (please refer to U.S. Pat. No. 6,707,878 (Patent Document 3)).

In tomosynthesis radiography, it is known that the slice thickness of a generated slice image, in other words, the resolution of the slice image in the depth direction of a subject (the direction in which radiation propagates) depends on a slice angle adopted at the time of radiography (please refer to T. Shiomi, "The principle and clinical application of Tomosynthesis", Journal of Japanese Society of Medical Imaging and Information Sciences, vol. 24, No. 2, pp. 22-27, 2007 (Non-Patent Document 1)). The slice angle refers to an angle formed, at a base point on a base plane (base surface), by lines connecting the base point and two end points that define the movement range of an X-ray tube. The base plane defines the range for obtaining slice images. For example, the base plane is a surface of an X-ray detector, a surface of the top board of a radiography table on which a subject (patient) is placed, a surface of a region of interest, the surface closest to the X-ray detector, when the region of interest has been set, an arbitrary cross section of the subject, or the like. According to Non-Patent Document 1, in radiographic images, the divisibility of an object in a subject in the thickness direction of the subject becomes higher as the slice angle is larger. Therefore, the slice thickness of a slice image becomes thinner. In contrast, in radiographic images, the divisibility of an object in a subject in the thickness direction of the subject becomes lower as the slice angle is smaller. Therefore, the slice thickness of the slice image becomes thicker.

In tomosynthesis radiography, X-rays that are output from each radiation source position to a subject disperse in cone form. Therefore, if a position in the depth direction of the subject differs, the slice angle differs. Therefore, if all of radiographic images obtained by radiography are used to generate a slice image of each slice plane, the slice angle differs depending on the position in the depth direction of the slice plane. Consequently, the slice thickness of each of the slice images generated on respective slice planes differs from each other.

SUMMARY OF THE INVENTION

In view of the foregoing circumstances, it is an object of the present invention to make it possible to generate slice images that have substantially the same slice thickness in tomosynthesis radiography, regardless of the position of the slice plane.

A radiography apparatus according to the present invention is a radiography apparatus comprising:

a radiation source that outputs radiation to a subject;

a detection means that detects the radiation that has passed through the subject;

an image obtainment means that moves, relative to the detection means, the radiation source in a movement range that is calculated based on a desired slice angle with respect to a predetermined base point on a base plane that defines a range of obtaining a slice image of the subject, thereby moving the radiation source to a plurality of positions, and that obtains a plurality of radiographic images of the subject corresponding to the plurality of positions by irradiating the subject with radiation from the plurality of positions;

an image reconstruction means that reconstructs the slice image from the plurality of radiographic images; and a selection means that selects, based on a distance from a detection surface of the detection means to a slice plane on which the slice image is generated and the desired slice angle, radiographic images to be used to reconstruct the slice image.

The "base plane that defines a range of obtaining a slice image" may be a surface of a top board (top plate) of a radiography table on which a subject (patient) is placed, for example. Alternatively, the "base plane" may be a detection surface of a detection means, or a surface of a region of interest, the surface closest to the detection means, when the region of interest has been set, or an arbitrary cross section of the subject, or the like. Further, the "region of interest" is a region in which the degree of interest is particularly high when images are used for diagnosis. The "region of interest" is a target region in which slice images are obtained in the subject. In the present invention, the region of interest is a three-dimensional region defined by a range in the depth direction of the subject (in other words, the direction in which radiation propagates) and a range in an in-plane direction of the subject, which is perpendicular to the depth direction. Alternatively, a two-dimensional region on the base plane may be set as the region of interest.

The term "desired slice angle" refers to an angle formed, at a base point on a base plane, by lines connecting the base point and two end points that define the movement range of a radiation source.

Further, the expression "moves, relative to the detection means, the radiation source" refers to the case of moving only the radiation source while the detection means is being fixed and the case of moving both of the detection means and the radiation source in such a manner that they are synchronized with each other.

In the radiography apparatus of the present invention, the selection means may select the radiographic images to be Used to reconstruct the slice image also based on a position on the slice plane on which the slice image is generated.

The radiography apparatus of the present invention may further include an arithmetic operation means that calculates the movement range of the radiation source based on a distance between the base plane and the radiation source and the desired slice angle with respect to the predetermined base point on the base plane.

In the radiography apparatus of the present invention, the selection means may calculate a range of selecting radiographic images in the movement range of the radiation source based on a distance between the slice plane on which the slice image is generated and the radiation source and the desired slice angle with respect to a corresponding base point on the slice plane, the corresponding base point corresponding to the predetermined base point on the base plane. Further, the selection means may select the radiographic images that have been obtained when the radiation source is located in the range of selecting radiographic images.

Further, the radiography apparatus of the present invention may include an arithmetic operation means that calculates the movement range of the radiation source based on a distance between the base plane and the radiation source and the desired slice angle with respect to each of two end points in a predetermined region on the base plane, the two end points being located at farthest positions from each other in the movement direction of the radiation source.

In the radiography apparatus of the present invention, the selection means may calculate a range of selecting radiographic images in the movement range of the radiation source based on a distance between the slice plane on which the slice image is generated and the radiation source and the desired slice angle with respect to a reconstruction point that reconstructs the slice image on the slice plane. Further, the selection means may select the radiographic images that have been obtained when the radiation source is located in the range of selecting the radiographic images.

In the radiography apparatus of the present invention, the base plane may be a surface of a top board on which the subject is placed or a surface of a region of interest in the subject, the surface of the region of interest being closest to the detection means.

According to the present invention, radiographic images that are used to reconstruct a slice image are selected based on a distance between a slice plane on which a slice image is generated and a detection surface of a detection means and a desired slice angle. Therefore, it is possible to calculate a range in the movement range of the radiation source, the range being defined by a certain slice angle (i.e., a desired slice angle) with respect to a corresponding base point on a slice plane, which corresponds to a predetermined base point on a base plane, regardless of the position of the slice plane in the depth direction. Further, it is possible to reconstruct a slice image by using only the radiographic images obtained in the calculated range. Therefore, it is possible to generate slice images having substantially the same slice thickness, regardless of the positions of the slice planes in the depth direction.

In this case, the movement range of the radiation source is calculated based on the distance between the base plane and the radiation source and the desired slice angle with respect to a predetermined base point on the base plane. Therefore, it is possible to obtain radiographic images in a range that is sufficient to generate a slice image.

Further, radiographic images that are used to reconstruct a slice image are selected also based on a position on a slice plane on which a slice image is generated. Therefore, it is possible to calculate a range in the movement range of the radiation source, the range that is defined by a certain slice angle (i.e., a desired slice angle) with respect to a reconstruction point that reconstructs a slice image on a slice plane, regardless of the position of the slice plane in the depth direction and a position on the slice plane in a direction perpendicular to the depth direction. Further, a slice image is reconstructed by using the radiographic images obtained in the calculated range. Therefore, it is possible to generate slice images having substantially the same slice thicknesses, regardless of the positions of the slice planes in the depth direction and a position on the slice plane in a direction perpendicular to the depth direction.

In this case, the movement range of the radiation source is calculated based on the distance between the base plane and the radiation source and the desired slice angle with respect to each of two predetermined base points in a predetermined region on the base plane, the two predetermined base points being located at farthest positions from each other in the movement direction of the radiation source. Therefore, it is possible to obtain radiographic images in a range that is sufficient to generate a slice image.

DESCRIPTION OF THE PREFERRED EMBODIMENTS

Figure 1:
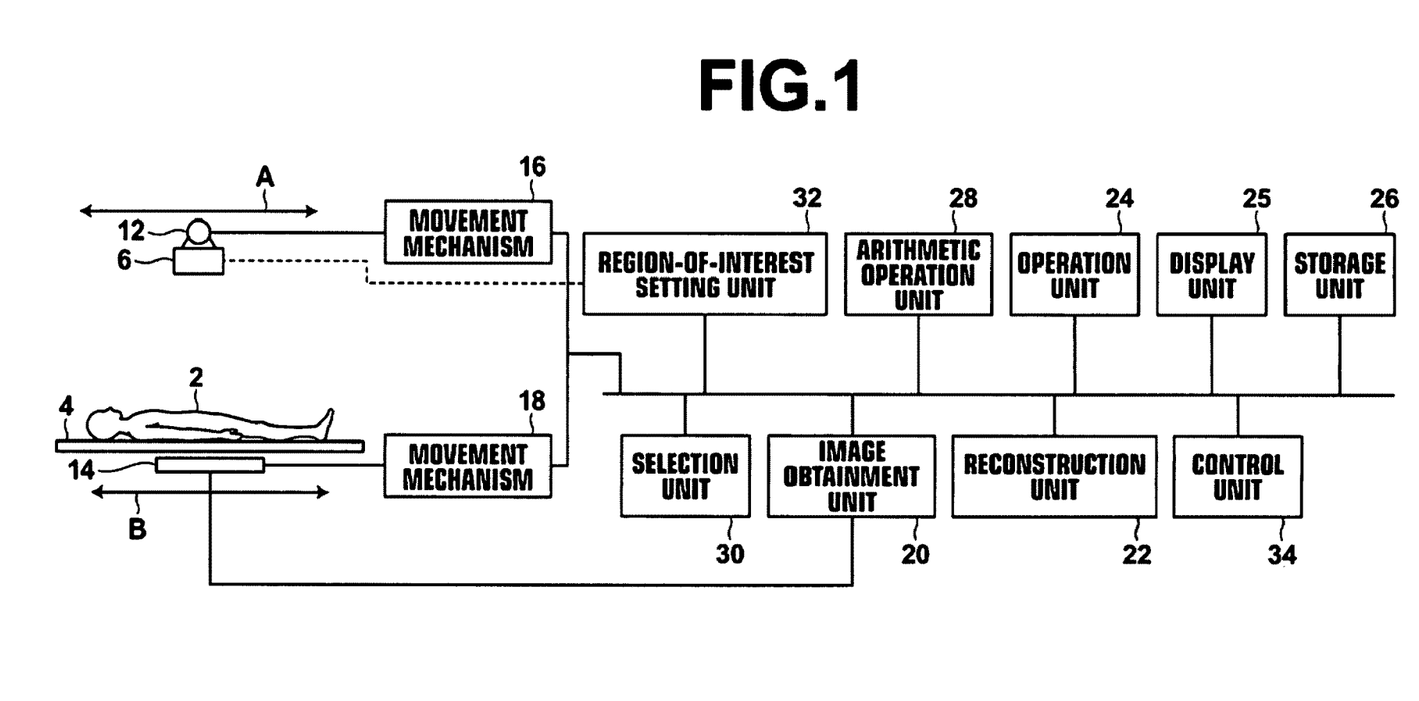
FIG. 1 is a schematic diagram illustrating the configuration of an X-ray radiography apparatus to which a radiography apparatus according to a first embodiment of the present invention is applied.

Hereinafter, embodiments of the present invention will be described with reference to drawings. FIG. 1 is a schematic diagram illustrating an X-ray radiography apparatus to which a radiography apparatus according to a first embodiment of the present invention has been applied. As illustrated in FIG. 1, an X-ray radiography apparatus 10 according to the present embodiment includes an X-ray tube 12 and a flat-panel X-ray detector (hereinafter, simply referred to as a detector) 14. The X-ray tube 12 is moved straight or along an arc or curve by a movement mechanism 16. The X-ray tube 12 outputs, at a plurality of positions on the movement path thereof, X-rays to a subject 2 on the top board 4 of a radiographic table. In the present embodiment, it is assumed that the X-ray tube 12 moves along a straight line in the direction of arrow A. The dose of radiation of X-rays output to the subject 2 is controlled by a control unit, which will be described later, so that the dose of radiation becomes a predetermined value. Further, a collimator (a diaphragm for changing an irradiation field size) 6 is connected to the X-ray tube 12 so that an operator can set the range of the subject 2 irradiated with radiation.

The detector 14 is arranged in such a manner to face the X-ray tube 12 with the top board 4 of the radiographic table, on which the subject 2 is placed, therebetween. The detector 14 is arranged so as to detect X-rays that have passed through the subject 2. The detector 14 is moved straight or in an arc or curve as necessary by a movement mechanism 18, and detects X-rays that have passed through the subject 2 at a plurality of positions on the movement path of the detector 14. In the present embodiment, it is assumed that the detector 14 is moved in the direction of arrow B along a straight line.

The X-ray radiography apparatus 10 includes an image obtainment unit 20 and a reconstruction unit 22. The image obtainment unit 20 moves the X-ray tube 12 along a straight line, and obtains a plurality of radiographic images of the subject 2 by irradiating the subject 2 with X-rays from different angles by the X-ray tube 12 located at a plurality of positions in the movement path of the X-ray tube 12, and by detecting X-rays that have passed through the subject 2 by the detector 14. The reconstruction unit 22 reconstructs a slice image representing a desired cross section of the subject 2 from the plurality of radiographic images obtained by the image obtainment unit 20. The method for reconstructing a slice image will be described.

Figure 2:
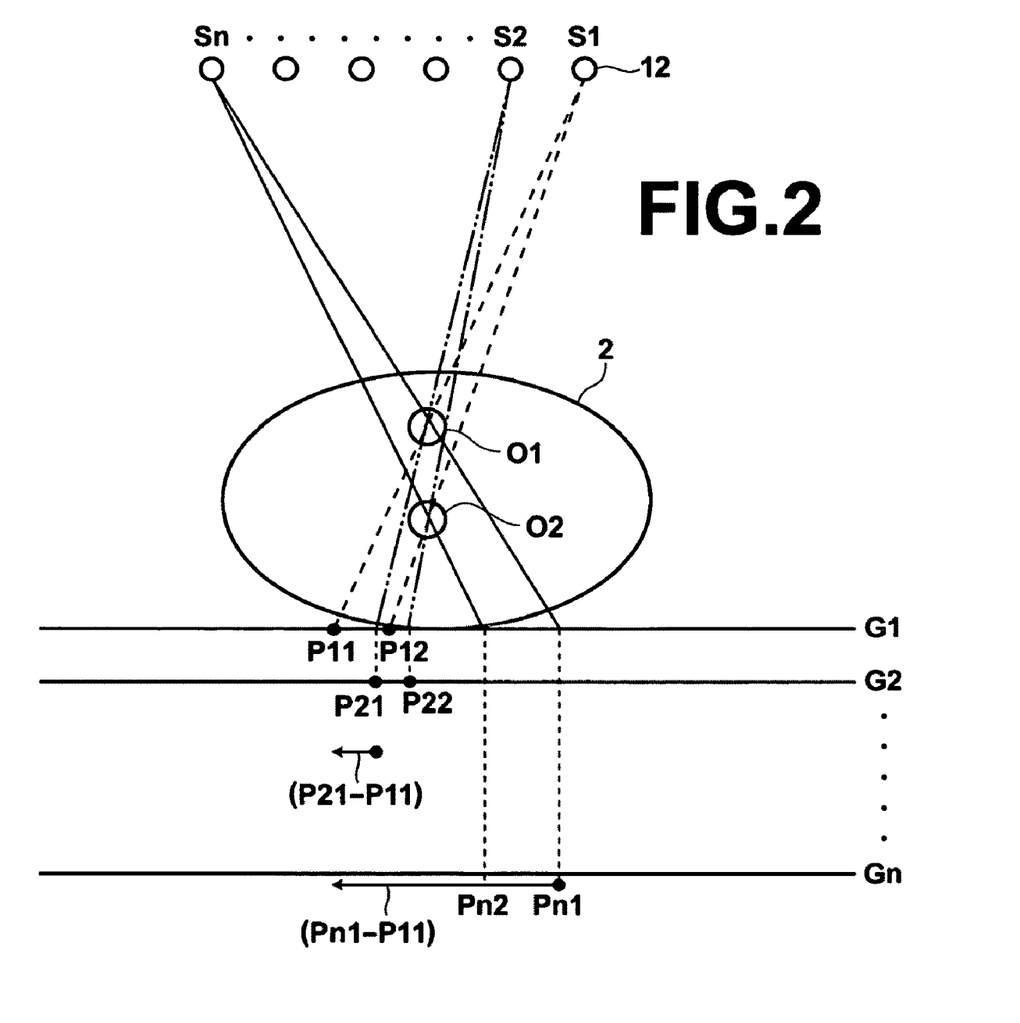
FIG. 2 is a diagram for explaining tomosynthesis radiography.

As illustrated in FIG. 2, when the X-ray tube 12 is moved to each position S1, S2, ..., Sn, and radiography is performed on the subject 2 from different irradiation angles, it is assumed that radiographic images G1, G2, ..., Gn are obtained when the X-ray tube 12 are located at positions S1, S2, ..., Sn, respectively. For example, when objects (O1, O2), which are located in a subject 2 at different depths from each other, are projected from position S1, at which the X-ray tube 12 is located, the objects (O1, O2) are projected to positions P11 and P12 in the radiographic image G1, respectively. Further, when the objects (O1, O2) are projected from position S2, at which the X-ray tube 12 is located, the objects (O1, O2) are projected to positions P21 and P22 in the radiographic image G2, respectively. In this way, when projection of the objects (O1, O2) is repeated from different positions S1, S2, ..., Sn, at which the X-ray tube 12 is located, object O1 is projected to positions P11, P21, ..., Pn1, respectively, and object O2 is projected to positions P12, P22, ..., Pn2, respectively, in such a manner to correspond to the positions of the radiation source (X-ray tube 12).

When the cross section on which the object O1 is present should be emphasized, the radiographic image G2 is moved by (P21-P11), the radiographic image G3 is moved by (P31-P11), ..., the radiographic image Gn is moved by (Pn1-P11), and the moved radiographic images are added to generate a slice image in which a structure on the cross section at the depth of the object O1 is emphasized. Further, when the cross section on which the object O2 is present should be emphasized, the radiographic image G2 is moved by (P22-P12), the radiographic image G3 is moved by (P32-P12), ..., the radiographic image Gn is moved by (Pn2-P12), and the moved radiographic images are added. As described above, it is possible to obtain an image in which a slice image at a desired position is emphasized by matching the positions of the radiographic images G1, G2, ..., Gn based on the position of a necessary slice plane and by adding the radiographic images G1, G2, ..., Gn.

Further, the X-ray radiography apparatus 10 includes an operation unit 24, a display unit 25 and a storage unit 26. The operation unit 24 includes an input device, such as a keyboard, a mouse and a touch-panel-type device, and receives an instruction (information) for operating the X-ray radiography apparatus 10 from an operator. Further, the operation unit 24 receives an input of a desired slice angle that defines the range of obtaining slice images. In the present embodiment, each unit of the X-ray radiography apparatus 10 operates based on the information input by the operator at the operation unit 24. The display unit 25 is a display device, such as a liquid crystal monitor. The display unit 25 displays a radiographic image obtained by the image obtainment unit 20, and a slice image reconstructed by the reconstruction unit 22. Further, the display unit 25 displays a message necessary for operation, and the like. The storage unit 26 stores various kinds of parameters, or the like that are necessary to operate the X-ray radiography apparatus 10.

Figure 3:
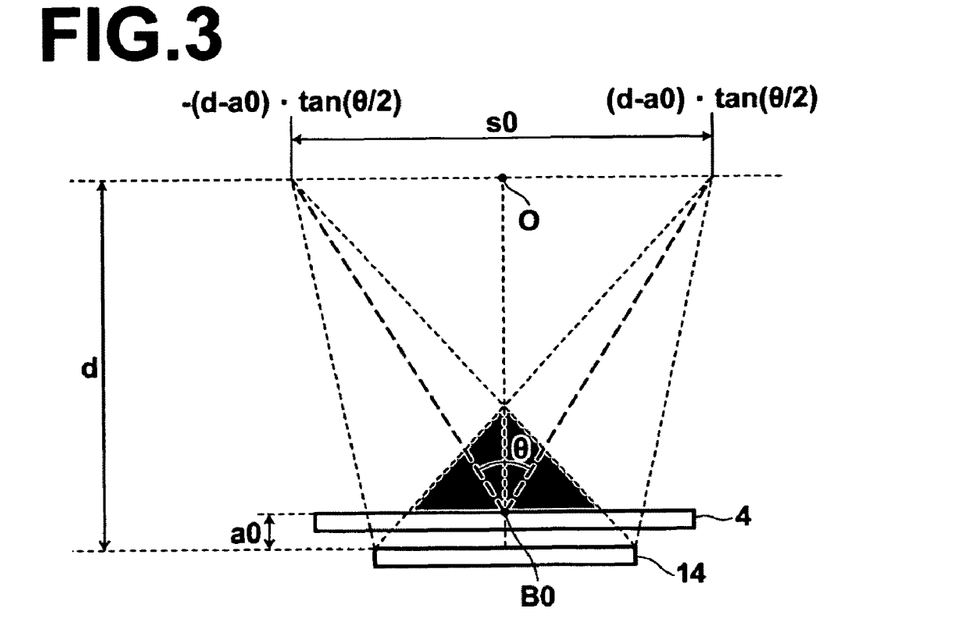
FIG. 3 is a diagram for explaining calculation of a movement range of an X-ray tube when a surface of a top board of a radiographic table is used as a base plane in the first embodiment.

Further, the X-ray radiography apparatus 10 includes an arithmetic operation unit 28. The arithmetic operation unit 28 calculates the movement range of the X-ray tube 12 based on a distance between a base plane and the X-ray tube 12 and a desired slice angle with respect to a predetermined base point on the base plane. FIG. 3 is a diagram for explaining calculation of the movement range of the X-ray tube 12 in the first embodiment. In FIG. 3, the base plane is the surface of the top board 4 of the radiography table. Here, the surface of the top board 4 of the radiography table and the detection surface of the detector 14 are parallel to the movement path of the X-ray tube 12. Therefore, a shortest distance between the movement path of the X-ray tube 12 and the surface of the top board 4 of the radiography table is a distance between the X-ray tube 12 and the surface of the top board 4 of the radiography table. Further, a shortest distance between the movement path of the X-ray tube 12 and the detection surface of the detector 14 is a distance between the X-ray tube 12 and the detection surface of the detector 14. Further, a slice plane, which will be described later, is also parallel to the movement path of the X-ray tube 12. Therefore, the shortest distance between the movement path of the X-ray tube 12 and the slice plane is a distance between the X-ray tube 12 and the slice plane. When the X-ray tube 12 moves along an arc, the longest distance between the movement path of the X-ray tube 12 and the slice plane is a distance between the X-ray tube 12 and the slice plane. Further, the longest distance between the movement path of the X-ray tube 12 and the surface of the top board 4 of the radiography table is a distance between the X-ray tube 12 and the surface of the top board 4 of the radiography table. Further, the longest distance between the movement path of the X-ray tube 12 and the detection surface of the detector 14 is a distance between the X-ray tube 12 and the detection surface of the detector 14.

In FIG. 3 and in the following descriptions, the movement range of the X-ray tube 12 is represented by s0, and a distance between the X-ray tube 12 and the detection surface of the detector 14 is represented by d. Further, a desired slice angle is represented by θ, and a distance between the detection surface of the detector 14 and a base plane (specifically, the surface of the top board 4 of the radiography table) is represented by a0. Further, a predetermined base point on the base plane is represented by B0. Here, an intersection of a perpendicular to the detector 14 that passes through the center of gravity of the detector 14 and the base plane is used as the base point B0. Further, the desired slice angle is input from the operation unit 24. The desired slice angle θ itself, or a so-called swing angle (which is θ/2) is input. In the present embodiment, the desired slice angle θ itself is input.

It is possible to calculate the movement range s0 of the X-ray tube 12, based on the relationship illustrated in FIG. 3, by using the distance d, the distance a0 and the desired slice angle θ. Specifically, when the intersection of the perpendicular to the detector 14 that passes through the base point B0 and the movement path of the X-ray tube 12 is origin O, the distance between the base plane and the X-ray tube is d-a0. Therefore, the arithmetic operation unit 28 calculates the movement range s0 of the X-ray tube 12, as $-(d-a0) \cdot \tan(\theta/2)$ through $(d-a0) \cdot \tan(\theta/2)$. Accordingly, both ends of the calculated movement range s0 are determined. Further, it is possible to obtain, as a region in which slice images are reconstructable in the X-ray radiography apparatus 10, a portion (indicated in gray) in which output ranges of X-rays to the detector 14 by the X-ray tube 12 located at the two ends overlap with each other.

Figure 4:
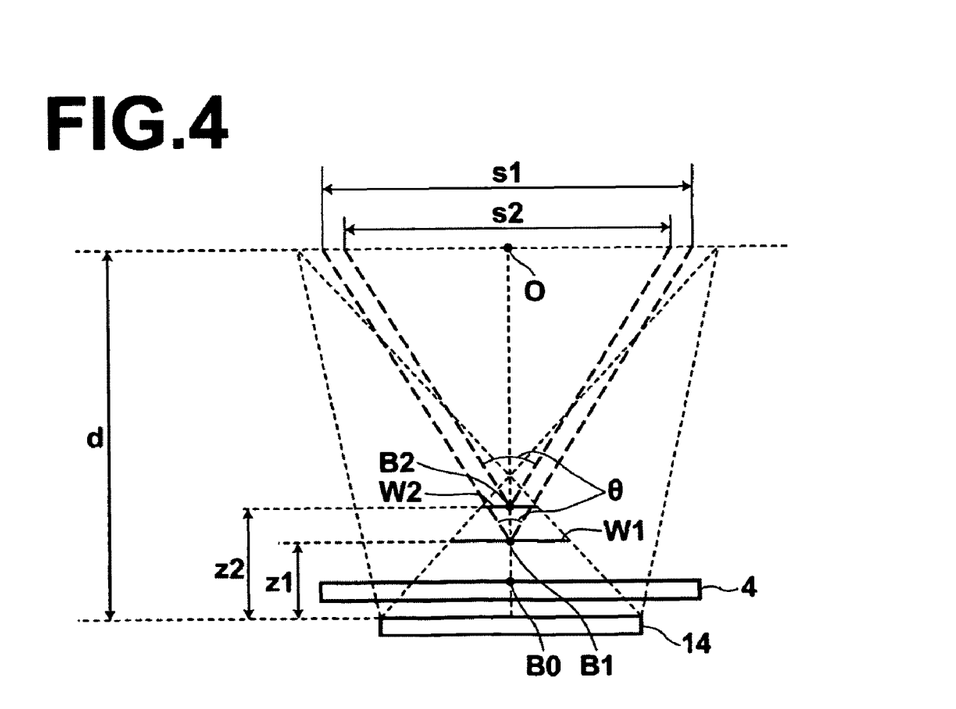
FIG. 4 is a diagram for explaining selection of radiographic images when a surface of a top board of a radiographic table is used as a base plane in the first embodiment.

Further, the X-ray radiography apparatus 10 includes a selection unit 30. The selection unit 30 selects radiographic images to be used when the reconstruction unit 22 reconstructs a slice image representing a slice plane. The selection unit 30 selects the radiographic images from all of the radiographic images obtained by the image obtainment unit 20. FIG. 4 is a diagram for explaining selection of radiographic images in the first embodiment when the surface of the top board 4 of the radiography table is the base plane. In FIG. 4, a distance from slice plane W1 on which a slice image is reconstructed to the detection surface of the detector 14 is z1 (>a0). Corresponding base point B1 on the slice plane W1, the corresponding base point B1 corresponding to the base point B0 on the top board 4 of the radiography table, is the intersection of the perpendicular to the detector 14 that passes through the center of gravity of the detector 14 and the slice plane W1.

Here, the slice thickness of the slice image reconstructed on the slice plane W1 and the slice thickness of the slice image reconstructed on the base plane, as a slice plane, become the same by generating the slice image on the slice plane W1 in the following manner. The slice image on the slice plane W1 is generated by calculating, as a range of selecting radiographic images in the movement range of the X-ray tube 12, a range defined by the desired slice angle θ with respect to the corresponding base point B1 on the slice plane W1, and by reconstructing the slice image representing the slice plane W1 from the radiographic images obtained when the X-ray tube 12 is located in the range of selecting the radiographic images.

Therefore, the selection unit 30 calculates, as the range s1 of selecting radiographic images, a range defined by the desired slice angle θ with respect to the corresponding base point B1 on the slice plane W1. The selection unit 30 calculates the range in the movement range of the X-ray tube 12 based on the distance d, the distance z1 and the desired slice angle θ. Further, the selection unit 30 selects radiographic images obtained when the X-ray tube 12 is located in the range s1 of selecting radiographic images. Since the distance between the slice plane W1 and the X-ray tube 12 is d-z1, the range s1 of selecting radiographic images is $-(d-z1) \cdot \tan(\theta/2)$ through $(d-z1) \cdot \tan(\theta/2)$.

With respect to slice plane W2, the distance z2 between the slice plane W2 and the detection surface of the detector 14 is larger than the distance z1 between the slice plane W1 and the detection surface of the detector 14 (z2>z1). The selection unit 30 calculates, as range s2 of selecting radiographic images in the movement range of the X-ray tube, a range defined by desired slice angle θ with respect to corresponding base point B2 on the slice plane W2. Since the distance between the slice plane W2 and the X-ray tube 12 is d-z2, the range s2 of selecting radiographic images is $-(d-z2) \cdot \tan(\theta/2)$ through $(d-z2) \cdot \tan(\theta/2)$.

Further, the X-ray radiography apparatus 10 includes a region-of-interest setting unit 32. The operator sets the range of the subject 2 with respect to the depth direction of the subject 2 (for example, a height from the top board of the radiographic table) by using the operation unit 24. Further, the operator sets the range of the subject 2 with respect to the in-plane direction, which is perpendicular to the depth direction, by using the collimator 6. When the operator sets the range by using the collimator 6, the subject 2 is illuminated with a beam of visible light through the collimator 6 instead of being irradiated with X-rays. Accordingly, the operator can set the range of the subject 2 with respect to the in-plane direction, which is perpendicular to the depth direction, by adjusting the range of visible light illuminating the subject 2 by using the collimator 6. The region-of-interest setting unit 32 sets a three-dimensional region of interest based on the range of the subject 2 with respect to the depth direction, which has been set by the operator by using the operation unit 24, and the range of the subject 2 with respect to the in-plane direction, which is perpendicular to the depth direction, the range being set by the operator by using the collimator 6. When the region of interest has been set, a plane (surface) in the region of interest, the plane being the closest to the detection surface of the detector 14, is the base plane.

Figure 5:
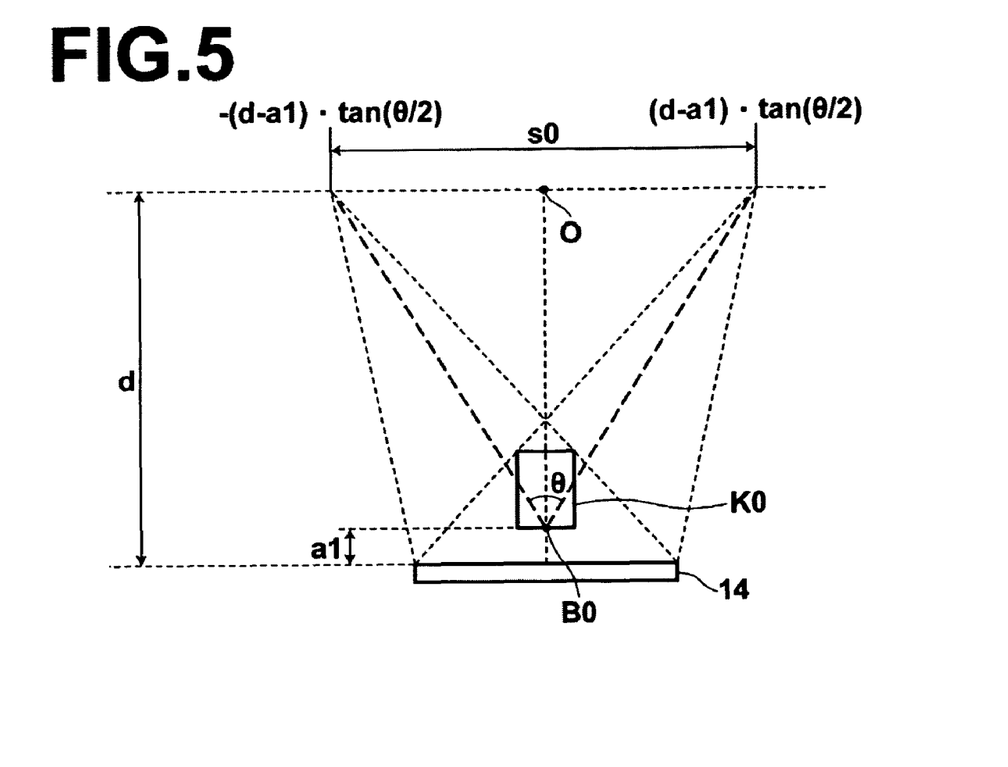
FIG. 5 is a diagram for explaining calculation of a movement range of the X-ray tube when a region of interest is set in the first embodiment.

Next, calculation of the movement range of the X-ray tube 12 when the region of interest has been set will be described. FIG. 5 is a diagram for explaining calculation of the movement range of the X-ray tube 12 when a region of interest has been set in the first embodiment. In FIG. 5, the region of interest is represented by K0. Further, a distance from a detection surface of the detector 14 to a plane in the region K0 of interest, the plane being the closest to the detection surface of the detector 14, is represented by a1 (in other words, the plane is a base plane). Further, an intersection of the perpendicular to the detector 14 that passes through the center of gravity of the detector 14 and the base plane is used as the predetermined base point B0 on the base plane in the region K0 of interest.

It is possible to calculate the movement range s0 of the X-ray tube 12, based on the relationship illustrated in FIG. 5, by using the distance d, the distance a1 and the desired slice angle θ. Specifically, when the intersection of the perpendicular to the detector 14 that passes through the base point B0 and the movement path of the X-ray tube 12 is origin O, the distance between the base plane and the X-ray tube is d−a1. Therefore, the arithmetic operation unit 28 calculates the movement range s0 of the X-ray tube 12, as −(d−a1)·tan(θ/2) through (d−a1)·tan(θ/2). Accordingly, the positions of both ends of the calculated movement range s0 are determined. Further, it is possible to obtain, as a region in which slice images are reconstructable in the X-ray radiography apparatus 10, a portion in which output ranges of X-rays to the detector 14 by the X-ray tube 12 located at the two ends overlap with each other.

Figure 6:
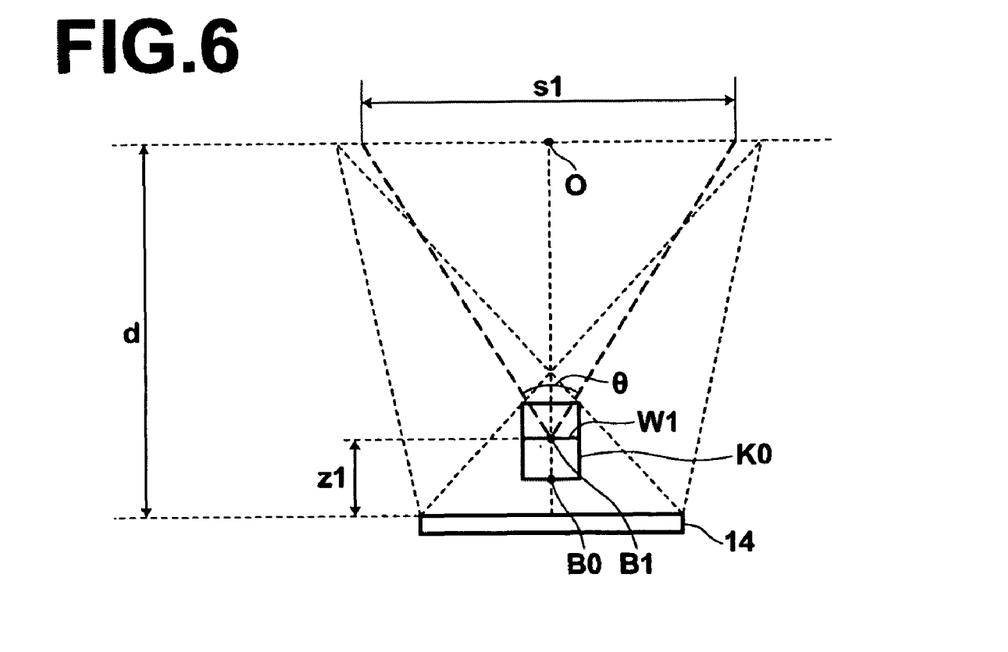
FIG. 6 is a diagram for explaining selection of radiographic images when a region of interest is set in the first embodiment.

FIG. 6 is a diagram for explaining selection of radiographic images when a region of interest has been set in the first embodiment. In FIG. 6, a distance from slice plane W1 in the region K0 of interest, on which a slice image is reconstructed, to the detection surface of the detector 14 is z1 (>a1). Corresponding base point B1 on the slice plane W1, the corresponding base point B1 corresponding to the base point B0 on the top board 4 of the radiography table, is the intersection of the perpendicular to the detector 14 that passes through the center of gravity of the detector 14 and the slice plane W1.

Here, the slice thickness of the slice image reconstructed to represent the slice plane W1 in the region K0 of interest and the slice thickness of the slice image reconstructed on the base plane, as a slice plane, become the same by generating the slice image on the slice plane W1 in the following manner. The slice image on the slice plane W1 is generated by calculating, as the range of selecting radiographic images, a range defined by the desired slice angle θ with respect to the corresponding base point B1 on the slice plane W1, and by reconstructing the slice image representing the slice plane W1 from the radiographic images obtained when the X-ray tube 12 is located in the range of selecting radiographic images.

Therefore, even when the region K0 of interest has been set, the selection unit 30 calculates, as the range s1 of selecting radiographic images in the movement range of the X-ray tube 12, a range defined by the desired slice angle θ with respect to the corresponding base point B1 on the slice plane W1. The selection unit 30 calculates the range s1 based on the distance d, the distance z1 and the desired slice angle θ. Further, the selection unit 30 selects radiographic images obtained when the X-ray tube 12 is located in the range s1 of selecting radiographic images. Since the distance between the slice plane W1 and the X-ray tube 12 is d−z1, the range s1 of selecting radiographic images is −(d−z1)·tan(θ/2) through (d−z1)·tan(θ/2).

Further, the X-ray radiography apparatus 10 includes a control unit 34 for controlling each unit of the X-ray radiography apparatus 10. The control unit 34 controls each unit of the X-ray radiography apparatus 10 based on an instruction from the operation unit 24.

Figure 7:
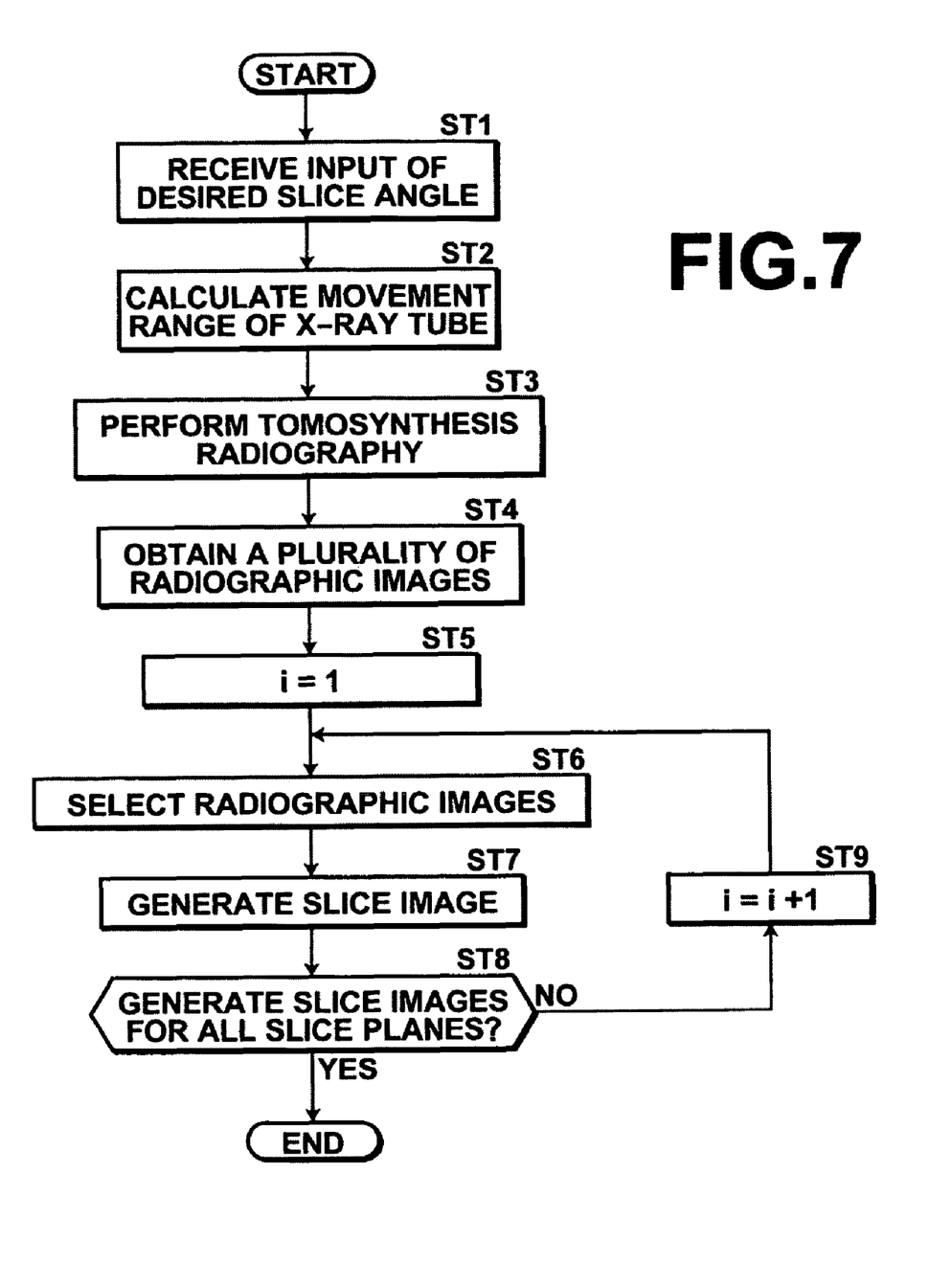
FIG. 7 is a flow chart illustrating a process performed in the first embodiment.

Next, processing performed in the first embodiment will be described. FIG. 7 is a flow chart illustrating the process performed in the first embodiment. First, the control unit 34 receives an input of desired slice angle θ by an operator at the operation unit 24 (step ST1). The arithmetic operation unit 28 calculates the movement range of the X-ray tube 12 by using the desired slice angle θ (step ST2). Further, the control unit 34 performs tomosynthesis radiography while moving the X-ray tube 12 in the calculated movement range (step ST3). The image obtainment unit 20 obtains a plurality of radiographic images (step ST4).

Next, the reconstruction unit 22 sets, as a first slice plane, a slice plane on which a slice image is to be generated (i=1, step ST5). The selection unit 30 selects radiographic images to be used to generate the slice image representing the set slice plane (step ST6). The reconstruction unit 22 reconstructs a slice image from the selected radiographic images (step ST7). The reconstruction unit 22 judges whether slice images representing all of slice planes have been generated (step ST8). If step ST8 is NO, the reconstruction unit 22 sets, as the next slice plane, a slice plane on which a slice image is to be generated (i=i+1, step ST9), and processing returns to step ST6. If step ST8 is YES, processing ends. Further, the generated slice images may be stored in a storage device, such as an HDD, which is not illustrated. Alternatively, the generated slice images may be sent to an external server through a network.

As described above, in the first embodiment, radiographic images to be used to reconstruct a slice image are selected based on a distance between the slice plane, on which the slice image is to be generated, and the detection surface of the detector 14 and the desired slice angle θ. Therefore, it is possible to calculate the range s1 of selecting radiographic images in the movement range of the X-ray tube 12, the range of selecting radiographic images that is defined by a certain slice angle (i.e., a desired slice angle θ) with respect to a predetermined base position on a slice plane, regardless of the position of the slice plane in the depth direction. Further, a slice image is reconstructed by using the radiographic images obtained in the calculated range. Therefore, it is possible to generate slice images having substantially the same slice thickness, regardless of the position of the slice plane in the depth direction.

Further, since the movement range s0 of the X-ray tube 12 is calculated based on the distance between the base plane and the X-ray tube 12 and the desired slice angle θ with respect to the predetermined base point B0 on the base plane, it is possible to obtain a sufficient range of radiographic images for generating a slice image.

Next, a second embodiment of the present invention will be described. An X-ray radiography apparatus in the second embodiment of the present invention is structured in the same manner as the X-ray radiography apparatus 10 according to the first embodiment, and only the processing performed in the apparatus of the second embodiment differs from the processing performed in the apparatus of the first embodiment. Therefore, detailed descriptions on the structure of the X-ray radiography apparatus of the second embodiment are omitted. The X-ray radiography apparatus 10 of the second embodiment differs from that of the first embodiment, in that in the second embodiment, the radiographic images to be used to reconstruct a slice image are selected not only based on the position of the slice plane, on which the slice image is generated, in the depth direction but also based on the position on the slice plane in a direction perpendicular to the depth direction.

Figure 8:
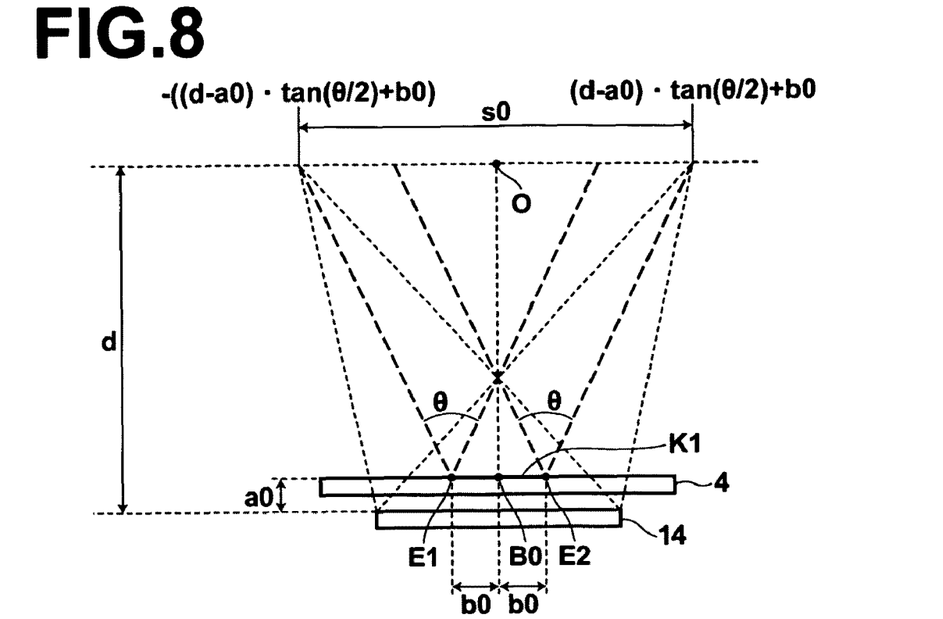
FIG. 8 is a diagram for explaining calculation of a movement range of the X-ray tube when a surface of a top board of a radiographic table is used as a base plane in a second embodiment.

Next, calculation of the movement range of the X-ray tube 12 in the second embodiment will be described. FIG. 8 is a diagram for explaining calculation of the movement range of the X-ray tube 12 in the second embodiment. In FIG. 8, the surface of the top board 4 of the radiography table is the base plane. In FIG. 8, the movement range of the X-ray tube 12 is represented by s0, and the distance between the X-ray tube 12 and the detection surface of the detector 14 is represented by d. Further, the desired slice angle is represented by θ, and the distance between the detection surface of the detector 14 and the base plane is represented by a0. In the second embodiment, region K1 of interest, which is a two-dimensional region, is set on the base plane. Two edges of the region K1 of interest in the movement direction of the X-ray tube 12 are E1 and E2. Further, a distance between the base point B0 and the edge E1 and a distance between the base point B0 and the edge E2 in the movement direction of the X-ray tube 12 are b0. An intersection of the perpendicular to the detector 14 that passes through the center of gravity of the detector 14 and the base plane is used as the predetermined base point B0 in the region K1 of interest.

In the second embodiment, the movement range s0 of the X-ray tube 12 is a range including both of the movement range calculated based on the edge E1 of the region K1 of interest and the movement range calculated based on the edge E2 of the region K1 of interest. When the intersection of the perpendicular to the detector 14 that passes through the base point B0 and the movement path of the X-ray tube 12 is origin O, the distance between the base plane and the X-ray tube 12 is d−a0. Therefore, the arithmetic operation unit 28 calculates the movement range s0 of the X-ray tube 12, as −((d−a0)·tan(θ/2)+b0) through ((d−a0)·tan(θ/2)+b0). Accordingly, both ends of the calculated movement range s0 are determined. Further, it is possible to obtain, as a region in which slice images are reconstructable in the X-ray radiography apparatus 10, a portion in which output ranges of X-rays to the detector 14 by the X-ray tube 12 located at the two ends overlap with each other.

Figure 9:
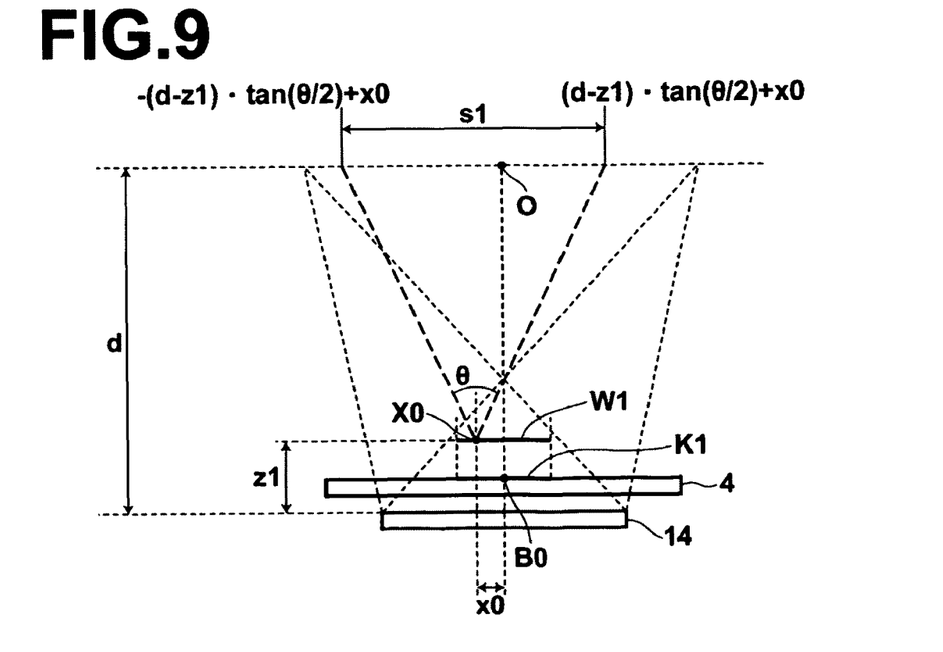
FIG. 9 is a diagram for explaining selection of radiographic images when a surface of a top board of a radiographic table is used as a base plane in the second embodiment.

Next, selection of radiographic images in the second embodiment will be described. FIG. 9 is a diagram for explaining selection of radiographic images in the second embodiment. In FIG. 9, a distance from slice plane W1, on which a slice image is reconstructed, to the detection surface of the detector 14 is z1 (>a0). A reconstruction point for reconstructing a slice image on the slice plane W1 is X0. Further, a distance from the intersection of the perpendicular to the detector 14 that passes through the center of gravity of the detector 14 and the slice plane W1 to the reconstruction point X0 in the movement direction of the X-ray tube 12 is x0. In the explanation of FIG. 9, the reconstruction point X0 is regarded as a point. However, in actual cases, the reconstruction point X0 is a row of linearly arranged pixels that extend in a direction perpendicular to the paper on which FIG. 9 is illustrated.

Here, the slice thickness of a pixel row in a slice image reconstructed at the reconstruction point X0 on the slice plane W1 and the slice thickness of the slice image on the base plane, as a slice plane, become the same by generating the slice image on the slice plane W1 in the following manner. The slice image on the slice plane W1 is generated by calculating, as the range of selecting radiographic images in the movement range of the X-ray tube 12, a range defined by the desired slice angle θ with respect to the reconstruction point X0 on the slice plane W1, and by reconstructing the slice image representing the slice plane W1 from the radiographic images obtained when the X-ray tube 12 is located in the range of selecting radiographic images.

Therefore, the selection unit 30 calculates, as the range s1 of selecting radiographic images in the movement range of the X-ray tube 12, a range defined by the desired slice angle θ with respect to the reconstruction point X0 on the slice plane W1. The selection unit 30 calculates the range s1 based on the distance d, the distance z1 and the desired slice angle θ. Further, the selection unit 30 selects radiographic images obtained when the X-ray tube 12 is located in the range s1 of selecting radiographic images. Since the distance between the slice plane W1 and the X-ray tube 12 is d−z1, the range s1 of selecting radiographic images is −(d−z1)·tan(θ/2)+x0 through (d−z1)·tan(θ/2)+x0.

Figure 10:
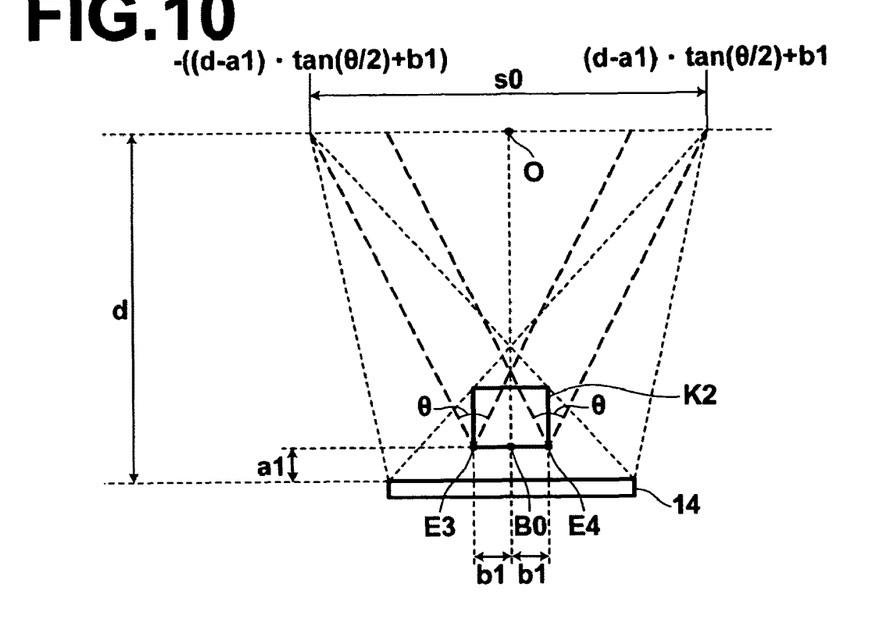
FIG. 10 is a diagram for explaining calculation of a movement range of the X-ray tube when a region of interest is set in the second embodiment.

Next, calculation of the movement range of the X-ray tube 12 when a three-dimensional region of interest has been set in the second embodiment will be described. FIG. 10 is a diagram for explaining calculation of the movement range of the X-ray tube 12 when a three-dimensional region of interest has been set in the second embodiment. In FIG. 10, a region of interest is represented by K2, and a distance from the detection surface of the detector 14 to a surface of the region K2 of interest, the surface being closest to the detection surface of the detector 14 (i.e., the surface of the region K2 of interest is a base plane), is a1. Further, two edges of the region K2 of interest in the movement direction of the X-ray tube 12 are E3 and E4. Further, a distance from the base point B0 to the edge E3 and a distance from the base point B0 to the edge E4 in the movement direction of the X-ray tube 12 are b1. Further, the intersection of the perpendicular to the detector 14 that passes through the center of gravity of the detector 14 and the base plane is used as the predetermined base point B0 in the region K2 of interest.

In the second embodiment, when the region K2 of interest has been set, the movement range of the X-ray tube 12 is a range in which both of the movement range calculated based on the edge E3 of the region K2 of interest and the movement range calculated based on the edge E4 of the region K2 of interest are combined with each other. Therefore, when the intersection of the perpendicular to the detector 14 that passes through the base point B0 and the movement path of the X-ray tube 12 is origin O, the distance between the base plane and the X-ray tube 12 is d−a1. Therefore, the arithmetic operation unit 28 calculates the movement range s0 of the X-ray tube 12, as −((d−a1)·tan(θ/2)+b1) through ((d−a1)·tan(θ/2)+b1). Accordingly, both ends of the calculated movement range s0 are determined. Further, it is possible to obtain, as a region in which slice images are reconstructable in the X-ray radiography apparatus 10, a portion in which output ranges of X-rays to the detector 14 by the X-ray tube 12 located at the two ends overlap with each other.

Figure 11:
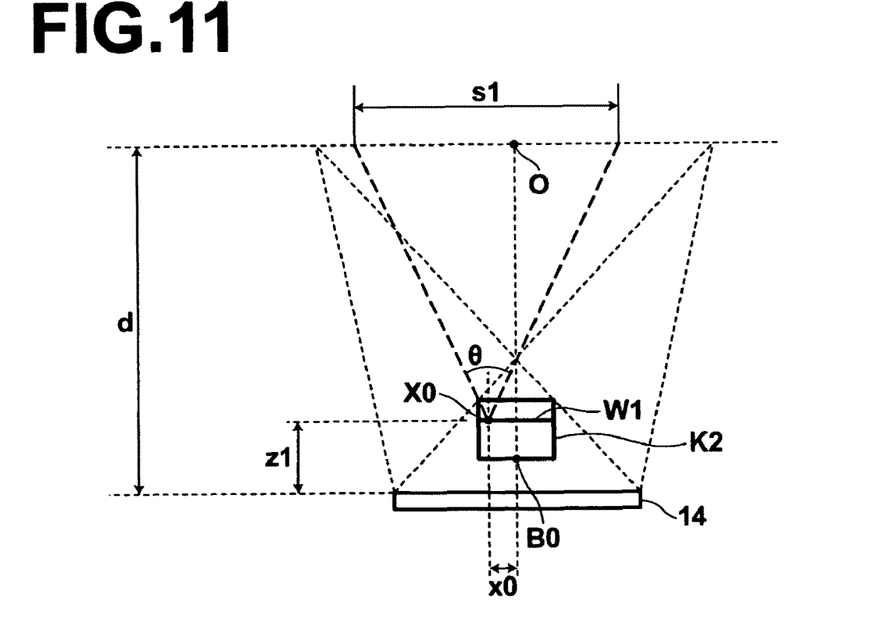
FIG. 11 is a diagram for explaining selection of radiographic images when a region of interest is set in the second embodiment.

Next, selection of radiographic images when a three-dimensional region of interest has been set in the second embodiment will be described. FIG. 11 is a diagram for explaining selection of radiographic images when a three-dimensional region of interest has been set in the second embodiment. In FIG. 11, a distance from slice plane W1, on which a slice image is reconstructed, to the detection surface of the detector 14 is z1 (>a1). A reconstruction point that reconstructs a slice image on the slice plane W1 is X0. Further, a distance from the intersection of the perpendicular to the detector that passes through the center of gravity of the detector 14 and the slice plane W1 to the reconstruction point X0 is x0. In the explanation of FIG. 11, the reconstruction point X0 is regarded as a point. However, in actual cases, the reconstruction point X0 is a row of linearly arranged pixels that extend perpendicularly to the paper on which FIG. 11 is illustrated.

Here, the slice thickness of a pixel row in the slice image reconstructed at reconstruction point X0 on the slice plane W1 and the slice thickness of the slice image on the base plane, as a slice plane, become the same by generating the slice image on the slice plane W1 in the following manner. The slice image on the slice plane W1 is generated by calculating, as the range of selecting radiographic images, a range defined by the desired slice angle θ with respect to the reconstruction point X0 on the slice plane W1, and by reconstructing the slice image on the slice plane W1 from the radiographic images obtained when the X-ray tube 12 is located in the range of selecting radiographic images.

Therefore, the selection unit 30 calculates, as the range s1 of selecting radiographic images in the movement range of the X-ray tube 12, a range defined by the desired slice angle θ with respect to the reconstruction point X0 on the slice plane W1. The selection unit 30 calculates the range s1 based on the distance d, the distance z1 and the desired slice angle θ. Further, the selection unit 30 selects radiographic images obtained when the X-ray tube 12 is located in the range s1 of selecting radiographic images. Since the distance between the slice plane W1 and the X-ray tube 12 is d−z1, the range s1 of selecting radiographic images is −(d−z1)·tan(θ/2)+x0 through (d−z1)·tan(θ/2)+x0.

Figure 12:
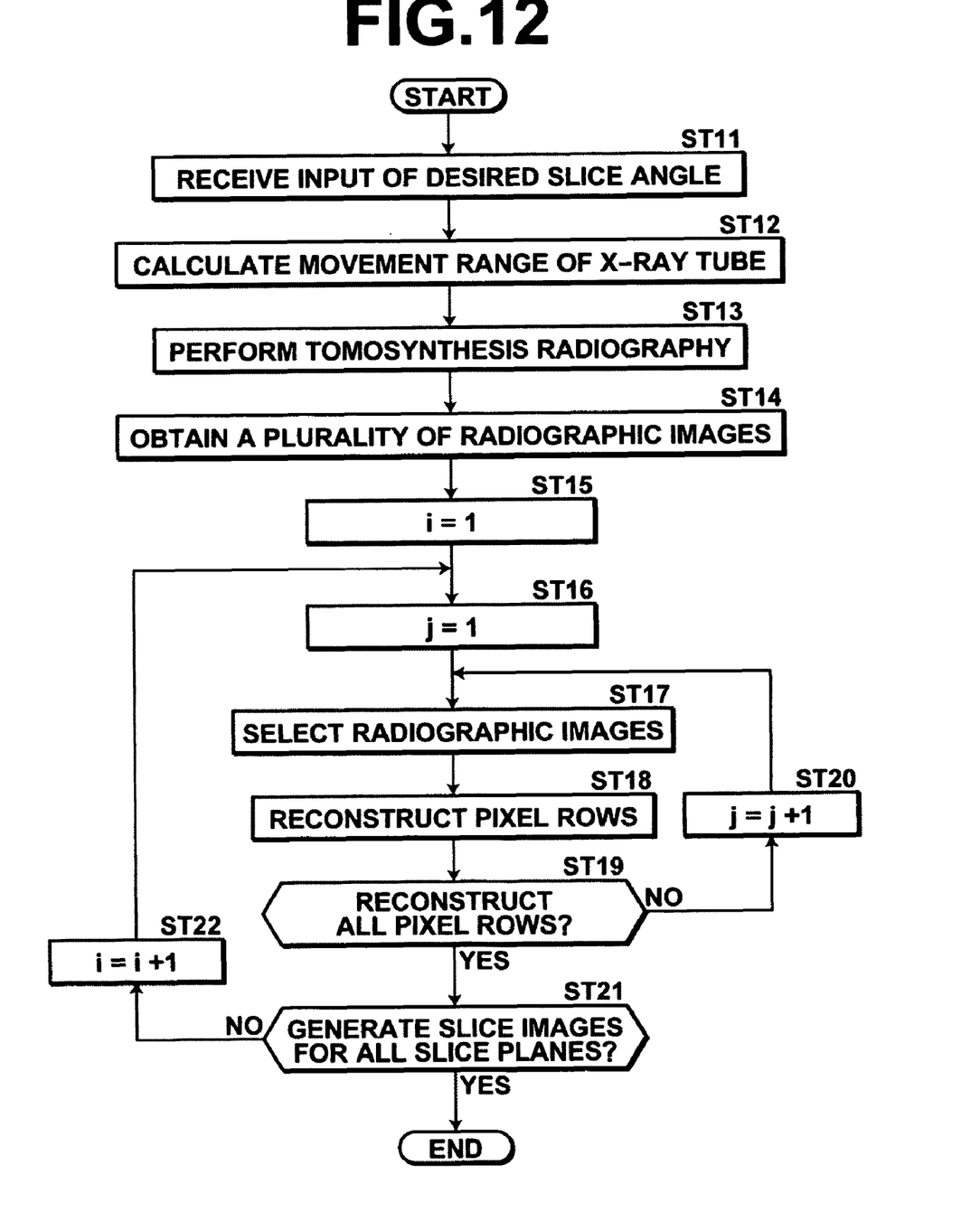
FIG. 12 is a flow chart illustrating a process performed in the second embodiment.

Next, processing performed in the second embodiment will be described. FIG. 12 is a flow chart illustrating the process performed in the second embodiment. First, the control unit 34 receives an input of desired slice angle θ by an operator at the operation unit 24 (step ST11). The arithmetic operation unit 28 calculates the movement range of the X-ray tube 12 by using the desired slice angle θ (step ST12). Further, the control unit 34 performs tomosynthesis radiography while moving the X-ray tube 12 in the calculated movement range (step ST13). The image obtainment unit 20 obtains a plurality of radiographic images (step ST14).

Next, the reconstruction unit 22 sets, as a first slice plane, a slice plane on which a slice image is to be generated (i=1, step ST15). Further, the reconstruction unit 22 sets, as a first pixel row, a pixel row that reconstructs a slice image on the slice plane (j=1, step 16). Further, the selection unit 30 selects radiographic images to be used to reconstruct the pixel row in the slice image on the slice plane (step ST17). The reconstruction unit 22 reconstructs the pixel row in the slice image from the selected radiographic images (step ST18). The reconstruction unit 22 judges whether all of pixel rows in the slice image have been reconstructed (step ST19). If step ST19 is NO, the reconstruction unit 22 sets, as the next pixel row, a pixel row that reconstructs the slice image (j=j+1, step ST20), and processing returns to step ST17.

If step ST19 is YES, the reconstruction unit 22 judges whether slice images for all of slice planes have been generated (step ST21). If step ST21 is NO, the reconstruction unit 22 sets, as the next slice plane, a slice plane on which a slice image is to be generated (i=i+1, step ST22), and the processing returns to step ST16. If step ST21 is YES, processing ends. The generated slice images are stored in a storage device, such as an HDD, which is not illustrated. Alternatively, the generated slice images may be sent to an external server through a network.

As described above, in the second embodiment, the radiographic images to be used to reconstruct a slice image are selected also based on a position on the slice plane, on which the slice image is to be generated. Therefore, it is possible to calculate a range of selecting radiographic images in the movement range of the X-ray tube 12, the range that is defined by a certain slice angle (i.e., a desired slice angle θ) with respect to a reconstruction point, which reconstructs a slice image on the slice plane, regardless of the position of the slice plane in the depth direction and the position on the slice plane in the direction perpendicular to the depth direction. Further, a slice image is reconstructed by using the radiographic images obtained at radiography positions in the calculated range. Therefore, it is possible to generate slice images having the same slice thickness, regardless of the position of the slice plane in the depth direction and the position on the slice plane in the direction perpendicular to the depth direction.

In the above embodiments, calculation of the movement range of the X-ray tube 12 and selection of radiographic images are performed by using the desired slice angle θ that is input by an operator. Alternatively, the movement range of the X-ray tube 12 may be calculated by using a slice angle that has been set in advance in the X-ray radiography apparatus 10, and the radiographic images may be selected.

In the above embodiments, only the X-ray tube 12 is moved. Alternatively, both of the X-ray tube 12 and the detector 14 may be moved in such a manner that they are synchronized with each other. In that case, the movement range of the X-ray tube 12 may be set in a manner similar to the first embodiment and the second embodiment. Further, the radiographic images to be used to reconstruct a slice image may be selected based on the position of the slice plane in the depth direction, or based on the position of the slice plane in the depth direction and the position on the slice plane in the direction perpendicular to the depth direction.

Figure 13:
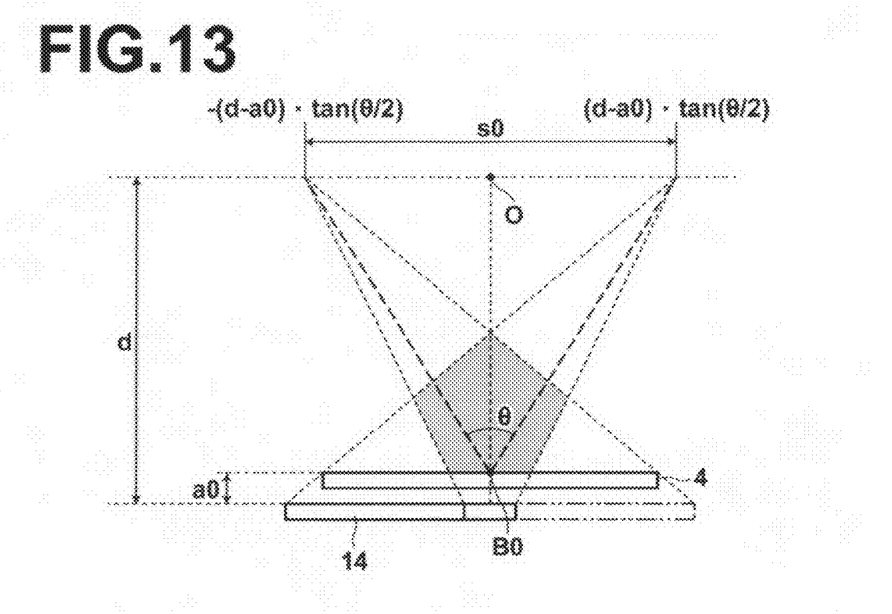
FIG. 13 is a diagram for explaining calculation of a movement range of the X-ray tube when the X-ray tube and a detector are moved in such a manner to be synchronized with each other in the first embodiment.
Figure 14:
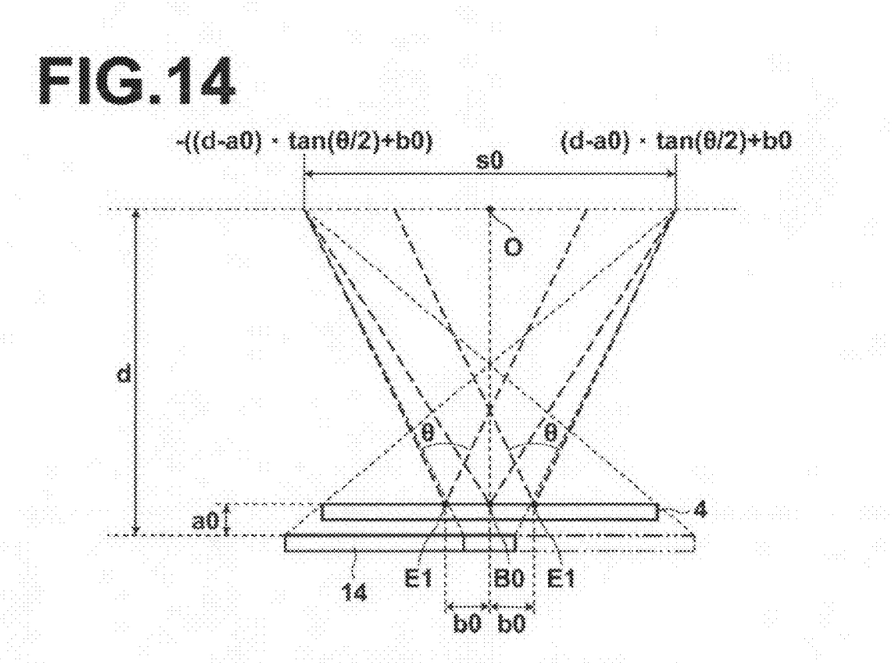
FIG. 14 is a diagram for explaining calculation of a movement range of the X-ray tube when the X-ray tube and a detector are moved in such a manner to be synchronized with each other in the second embodiment.

FIG. 13 is a diagram for explaining calculation of the movement range of the X-ray tube 12 when the X-ray tube 12 and the detector 14 are moved in such a manner that they are synchronized with each other in the first embodiment. FIG. 14 is a diagram for explaining calculation of the movement range of the X-ray tube 12 when the X-ray tube 12 and the detector 14 are moved in such a manner that they are synchronized with each other in the second embodiment. As illustrated in FIGS. 13 and 14, even when the X-ray tube 12 and the detector 14 are moved in such a manner to be synchronized with each other, the calculated movement range of the X-ray tube 12 is the same as the range calculated when only the X-ray tube 12 is moved. Further, in the case of setting a region of interest (not illustrated), the calculated movement range of the X-ray tube 12 when both of the X-ray tube 12 and the detector 14 are moved is the same as the movement range of the X-ray tube 12 when only the X-ray tube 12 is moved. However, when both of the X-ray tube 12 and the detector are moved, a portion (indicated in gray) in which output ranges of X-rays to the detector 14 by the X-ray tube 12 located at the two ends of the calculated movement range s0 overlap with each other is larger than a corresponding portion when only the X-ray tube 12 is moved. Therefore, it is possible to increase a region in which a slice image is reconstructable in the radiography apparatus 10 by moving the X-ray tube 12 and the detection 14 in such a manner that they are synchronized with each other, compared with the case of moving only the X-ray tube 12.

When the X-ray tube 12 and the detector 14 are moved in such a manner to be synchronized with each other, the radiographic images to be used to reconstruct a slice image may be selected in a manner similar to the first embodiment and the second embodiment.

In the first and second embodiments, tomosynthesis radiography is performed on a subject (patient) who is placed, in decubitus position, on the radiographic table. Needless to say, the present invention may be applied to tomosynthesis radiography using a radiographic table for standing position.

What is claimed is:

1. A radiography apparatus comprising:
    a radiation source that outputs radiation to a subject;
    a detection means that detects the radiation that has passed through the subject;
    an image obtainment means that moves, relative to the detection means, the radiation source in a movement range that is calculated based on a desired slice angle with respect to a predetermined base point on a base plane that defines a range of obtaining a slice image of the subject, thereby moving the radiation source to a plurality of positions, and that obtains a plurality of radiographic images of the subject corresponding to the plurality of positions by irradiating the subject with radiation from the plurality of positions;

an image reconstruction means that reconstructs the slice image from the plurality of radiographic images; and a selection means that selects, based on a distance from a detection surface of the detection means to a slice plane on which the slice image is generated and the desired slice angle, radiographic images to be used to reconstruct the slice image.

2. A radiography apparatus, as defined in claim 1, wherein the selection means selects the radiographic images to be used to reconstruct the slice image also based on a position on the slice plane, on which the slice image is generated.

3. A radiography apparatus, as defined in claim 2, further comprising:

an arithmetic operation means that calculates the movement range of the radiation source based on a distance between the base plane and the radiation source and the desired slice angle with respect to each of two end points in a predetermined region on the base plane, the two end points being located at farthest positions from each other in the movement direction of the radiation source.

4. A radiography apparatus, as defined in claim 3, wherein the selection means calculates a range of selecting radiographic images in the movement range of the radiation source based on a distance between the slice plane, on which the slice image is generated, and the radiation source and the desired slice angle with respect to a reconstruction point that reconstructs the slice image on the slice plane, and selects the radiographic images that have been obtained when the radiation source is located in the range of selecting the radiographic images.

5. A radiography apparatus, as defined in claim 2, wherein the selection means calculates a range of selecting radiographic images in the movement range of the radiation source based on a distance between the slice plane, on which the slice image is generated, and the radiation source and the desired slice angle with respect to a reconstruction point that reconstructs the slice image on the slice plane, and selects the radiographic images that have been obtained when the radiation source is located in the range of selecting the radiographic images.

6. A radiography apparatus, as defined in claim 1, further comprising:

an arithmetic operation means that calculates the movement range of the radiation source based on a distance between the base plane and the radiation source and the desired slice angle with respect to the predetermined base point on the base plane.

7. A radiography apparatus, as defined in claim 6, wherein the selection means calculates a range of selecting radiographic images in the movement range of the radiation source based on a distance between the slice plane, on which the slice image is generated, and the radiation source and the desired slice angle with respect to a corresponding base point on the slice plane, the corresponding base point corresponding to the predetermined base point on the base plane, and selects the radiographic images that have been obtained when the radiation source is located in the range of selecting the radiographic images.

8. A radiography apparatus, as defined in claim 1, wherein the selection means calculates a range of selecting radiographic images in the movement range of the radiation source based on a distance between the slice plane, on which the slice image is generated, and the radiation source and the desired slice angle with respect to a corresponding base point on the slice plane, the corresponding base point corresponding to the predetermined base point on the base plane, and selects the radiographic images that have been obtained when the radiation source is located in the range of selecting the radiographic images.

9. A radiography apparatus, as defined in claim 1, wherein the base plane is a surface of a top board on which the subject is placed, or a surface of a region of interest in the subject, the surface of the region of interest being closest to the detection means.

* * * * *